(12) United States Patent
Chang et al.

(10) Patent No.: US 7,273,474 B2
(45) Date of Patent: Sep. 25, 2007

(54) FLEXIBLE SUBSTRATE STRUCTURE FOR MICRONEEDLE ARRAYS AND ITS MANUFACTURING METHOD

(75) Inventors: Kai-Cheng Chang, Taipei (TW); Guang-Chyeng Fan, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 226 days.

(21) Appl. No.: 10/462,628

(22) Filed: Jun. 17, 2003

(65) Prior Publication Data
US 2004/0260251 A1    Dec. 23, 2004

(51) Int. Cl.
*A61M 5/32*    (2006.01)
(52) U.S. Cl. ...................................................... 604/272
(58) Field of Classification Search ................ 604/272, 604/20, 22, 35, 46, 501, 506, 181, 183, 239, 604/261, 191, 186; 216/75, 100, 102
See application file for complete search history.

(56) References Cited

U.S. PATENT DOCUMENTS 6,334,856 B1 *  1/2002  Allen et al. .................. 604/191
6,652,478 B1    11/2003  Gartstein et al. ............. 604/22

* cited by examiner

*Primary Examiner*—Manuel Mendez
(74) *Attorney, Agent, or Firm*—Troxell Law Office, PLLC

(57) ABSTRACT

The present invention is related to a flexible substrate structure for microneedle arrays and its manufacturing method, whose structure mainly comprising: tapered shape objects and flexible substrate. Wherein, structure of the tapered shape object is composed of a tip, sidewalls, and a base. Meanwhile, the flexible substrate winds tightly around sidewalls of tapered shape objects and is set up on, yet covers the base surface of tapered shape object which faces the tip of tapered shape object. Because the structure applies a flexible substrate along with tapered shape objects, hence, the fit-to-body capability is increased and allows thereof more appropriate for backside drug delivery, as well as sufficiently bring the characteristic of large-area manufacturing into full play.

6 Claims, 7 Drawing Sheets

FLEXIBLE SUBSTRATE STRUCTURE FOR MICRONEEDLE ARRAYS AND ITS MANUFACTURING METHOD

BACKGROUND OF THE INVENTION

The present invention is related to a structure of microneedle arrays and its manufacturing method, especially to a flexible substrate structure for microneedle arrays and its manufacturing method.

DESCRIPTION OF THE PRIOR ART

Nowadays, micro-electromechanical system is a newly developed area of study that every country in the world zealously engages in. Thus, its definition is various in different regions on earth. In Europe, it is called microsystem technology, MST, and is defined as an intelligent miniature system comprising functions such as sensing, processing and enabling, and is a one-chip or multi-chip system integrating two or more functions of electronics, mechanics, optics, chemistry, biology, magnetism or other qualities. In United State of American, it is called microelectromechanical system, MEMS, and is defined as an integrated micro-device or a system comprising electronic and mechanical parts that are fabricated using IC compatible batch-processing techniques, and size of the device or system is ranged from micrometer to millimeter. In Japan, it is called micro-machines, and is defined as a small sized device with functional parts that has a capability of executing complex and minute works.

The present invention is focused on structures of microneedle arrays with flexible substrate that are fabricated using micro-electromechanical technique. Nowadays, the so call microneedle array is a structure of rigid substrate that sets up with array of tapered shape objects by way of a fabricating process. Because each tapered shape object can have an opening on it tip or can have a conductive material coated on its surface, hence, the structure is often used in patches for drug delivery or in detection of human body's micro-signals, etc.

Thus, structures of microneedle array according to the prior arts are just as the aforementioned, it is mainly structured by setting tapered shape objects on a rigid substrate, such as silicon or glass. Although the present microelectromechanical technique already able to integrate microneedle array into size ranging between 5~500 micrometers height, but the rigid substrate of microneedle arrays according to the prior arts can caused a lot of troubles in applications.

Please refer to FIG. 1A, which is a drawing depicting a structure of microneedle array according to U.S. Pat. No. 20020082543. That is, a tapered shape object 142 of microneedle array structure 100 is set up on a silicon substrate 132 (the tapered objects are usually made of silicon) with reference to FIG. 1A. Because the microneedle array structure 100 uses a rigid material to be its substrate 132, therefore, when the microneedle array structure 100 is used for drug delivering patch, it is going to result in medicine can not be effectively implanted into skin.

For the reason thereof, please refer to FIG. 1B. FIG. 1B is a simple schematic drawing depicting contacts between skin and a patch with microneedle array structure. As seen in FIG. 1B, because the rigid substrate 132 of patch with microneedle array structure 100 can not fit itself completely to surface of rough skin 150, hence, medicines carried within opening (not shown) located at tip of each tapered shape objects 142 setting up on substrate 132 can not be effectively implanted into skin.

However, besides a microneedle array structure using rigid substrate is unsuitable for fitting to rough surface, it is also unsuitable for other applications because of its rigid substrate.

Please refer to FIG. 2A, which is a simple schematic drawing depicting a micro apparatus according to U.S. Pat. No. 20020082543. A micro apparatus 210 is a kind of apparatus for implanting medicine into skin 256. Wherein, a groove 240 is formed on substrate 230 that can be used for accommodating medicine, and a lid 220 of the groove 240 is made of a kind of plastic which contains a finger cot 250 thereon. Therefore, while using this micro apparatus 210 to implant medicine into skin 256, a pressure is applied by inserting finger 264 into the finger cot 250 so as to force medicines to flow through apertures 260 between substrate 230 and tapered shape objects 262, and then by way of opening 258 on tip of the tapered shape object 262 to implant medicine into skin 256.

Within the micro apparatus 210, it is difficult to form apertures 260 between substrate 230 and tapered shape object 262. The reason is that, during the formation of tapered shape object 262 on substrate 230, tip of tapered shape objects 262 can form an opening by a micro-electromechanical fabricating process, but an additional fabricating process is needed in order to form an aperture between the opening of tapered shape object 262 and substrate 230. Therefore, it is difficult to form apertures 260 between substrate 230 and tapered shape objects 262, and the probability of success is low.

Moreover, when finger 264 applies a pressure on lid 220, not only the lid 220 is subjected to an external force, but also the substrate 230 is subjected to the external force. Please refer to FIG. 2B, which is a simple schematic drawing depicting the substrate 230 of FIG. 2A while subjecting to an external force. Since, in a micro-electromechanical fabricating process of microneedle array structure, the silicon usually used as substrate 230 is a kind of monocrystalline silicon that is easy to break. Thus, the substrate 230 is easy to crack by the impact of external forces. In the mean time, if the micro apparatus 210 uses a large-area substrate 230, the substrate 230 will become even more fragile.

Hence, microneedle array structures using rigid substrate indeed possess the following drawbacks:

1. Rigid substrate can not have a better fit-to-body capability.
2. Apertures are difficult to form between rigid substrate and tapered shape objects.
3. Rigid substrate is easy to crack by the impact of external forces.
4. Due to the fragility of rigid substrate, it can not be employed in large-area.

In view of the above, the present invention provides a flexible substrate structure for microneedle arrays and its manufacturing method, which not only can increase the fit-to-body capability, but also it is even more appropriate for backside drug delivery, as well as sufficiently bring the characteristic of large-area fabricating into full play.

SUMMARY OF THE INVENTION

The main objective of the present invention is to provide a flexible substrate structure for microneedle arrays, comprising mainly tapered shape objects and a flexible substrate. Wherein, structure of the tapered shape object is composed of a tip, sidewalls, and a base. Meanwhile, the flexible substrate is winded tightly around sidewalls of tapered shape object and is set up on, yet covers the base surface of tapered shape object facing the tip of the tapered shape object.

The secondary objective of the present invention is to provide another flexible substrate structure for microneedle arrays, also comprising mainly tapered shape objects and a flexible substrate. But surface of the tapered shape object possesses a conducting layer that extends along the sidewall of the tapered shape object to the base of the tapered shape object. And the flexible substrate is winded tightly around sidewalls of tapered shape object and is set up on, yet covers the base surface of tapered shape object facing the tip of tapered shape object. The flexible substrate is distributed just to expose the two ends of the conducting layer for signal transmitting.

In a preferred embodiment of the present invention, different source materials can be chosen for the flexible substrate structure for microneedle arrays corresponding to different applications. Take the tapered shape object for instance, when the flexible substrate structure for microneedle arrays is employed as drug delivery device, a tapered shape object with opening on its tip can be chosen.

The final objective of the present invention is to provide a fabricating method of flexible substrate structure for microneedle arrays, which comprising: First, carrying on with an ion implantation on tips of tapered shape objects, sidewall areas and base areas of tapered shape objects that are close to sidewalls of tapered shape objects. Secondly, applying the flexible substrate on surfaces of a part of sidewalls and on the bases of tapered shape objects facing the tips of tapered shape objects, so that the flexible substrate is winded tightly around sidewalls of tapered shape objects and is distributed on the bases of tapered shape objects. Finally, the tapered shape objects are etched so as to set up, yet cover the base surfaces of tapered shape objects that are close to sidewalls of tapered shape objects and face the tips of tapered shape objects with the flexible substrate.

In a preferred embodiment of the present invention, the fabricating method further includes: before carrying on with ion implantation, plating a conducting layer on sidewall surfaces of tapered shape objects and base surfaces of tapered shape objects facing tips of tapered shape objects, so as to transmit signals from the conducting layer on sidewall of tapered shape object to the conducting layer on base of tapered shape object.

The method for ion implantation further comprises: First, applying a layer of photoresist on tips of tapered shape objects, sidewall areas and base surface areas of tapered shape objects. Secondly, carrying on with exposures toward the photoresist on tips of tapered shape objects, sidewall areas and base surface areas of tapered shape objects that are close to sidewalls of tapered shape object. Finally, carrying on with developments toward the photoresist on tips of tapered shape objects, sidewall areas and base surface areas of tapered shape objects, so as to proceed with ion implantation.

Therein, the method for applying photoresist further includes employing photomask to define tips of tapered shape objects, sidewall areas and base surface areas of tapered shape objects that are close to sidewalls of tapered shape object so as to carry on with exposures toward the photoresist thereof.

As to the manufacturing method, after ion implantation, further comprises applying a layer of photoresist on tips of tapered shape objects, sidewall areas and base surface areas of tapered shape objects that are close to sidewalls of tapered shape object. Then, carrying on with exposures and developments toward the photoresist of base surface areas of tapered shape objects, so as to apply flexible substrate on the base surface areas of tapered shape objects that are close to sidewalls of tapered shape object.

In summary, the present invention provides a flexible substrate structure for microneedle arrays and its manufacturing method, which by way of the combination of tapered shape objects and flexible substrate, not only can increase its fit-to-body capability, but also enables thereof even more appropriate for backside drug delivery, as well as sufficiently bring the characteristic of large-area fabricating into full play.

DETAILED DESCRIPTION OF THE PREFERRED EMBODIMENT

For your esteemed members of reviewing committee to further understand and recognize the objectives, the characteristics, and the functions of the invention, a detailed description in matching with corresponding drawings are presented as the following.

In view of the monocrystalline silicon substrate used in the present microneedle arrays structure is easy to break. Besides the rigid substrate is easy to crack by impacts of external forces, when using this rigid substrate structure for microneedle array in patch system, it is troubled by worse fit-to-body capability, apertures are difficult to form, and not feasible in large-area fabrication. In addition, while employing a patch system using rigid substrate for microneedle arrays structure as drug delivery device, in order to insert medicine inside openings on tips of tapered shape objects for the purpose of drug delivery, the driving method and capacity thereof is a difficult technical task to accomplish. Therefore, the present invention intents to adopt flexible materials as substrates of microneedle arrays structures, and through the combination of tapered shape objects and flexible substrate, it can achieve purposes of backside drug delivery or specimens gathering, as well as a great potential in applications of microneedle arrays structures.

Figure 1A:
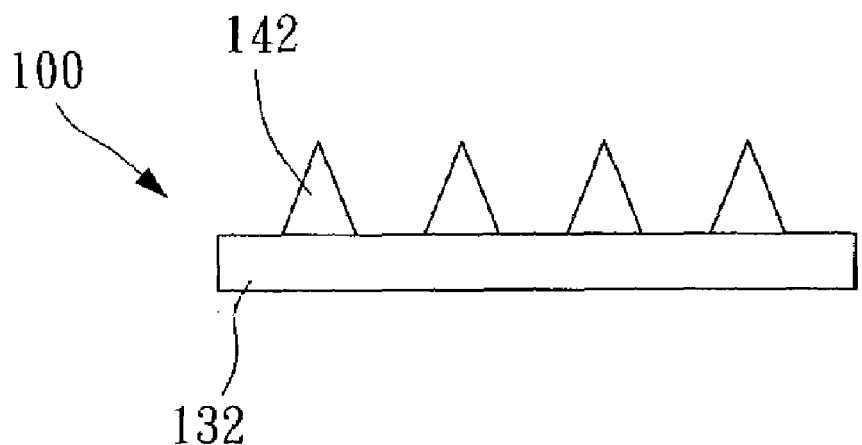
FIG. 1A is a microneedle array structure drawing according to U.S. Pat. No. 20020082543.
Figure 1B:
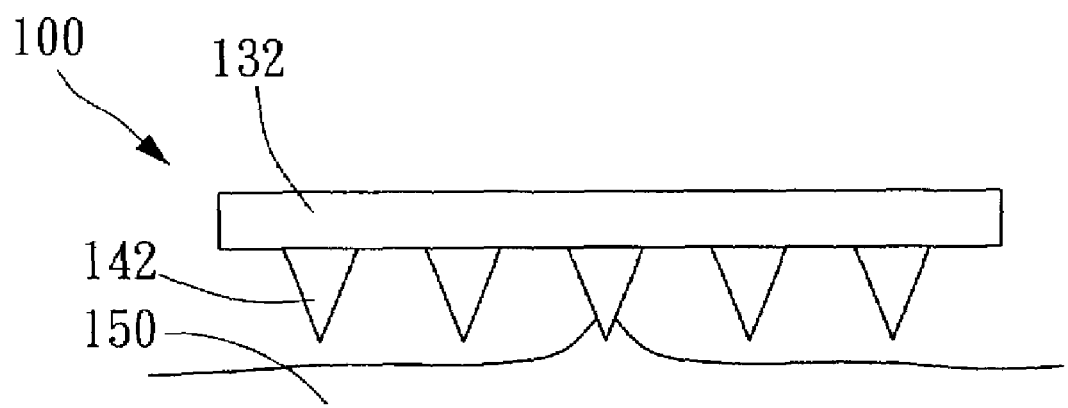
FIG. 1B is a simple schematic drawing depicting contacts between skin and a patch with microneedle array structure
Figure 2A:
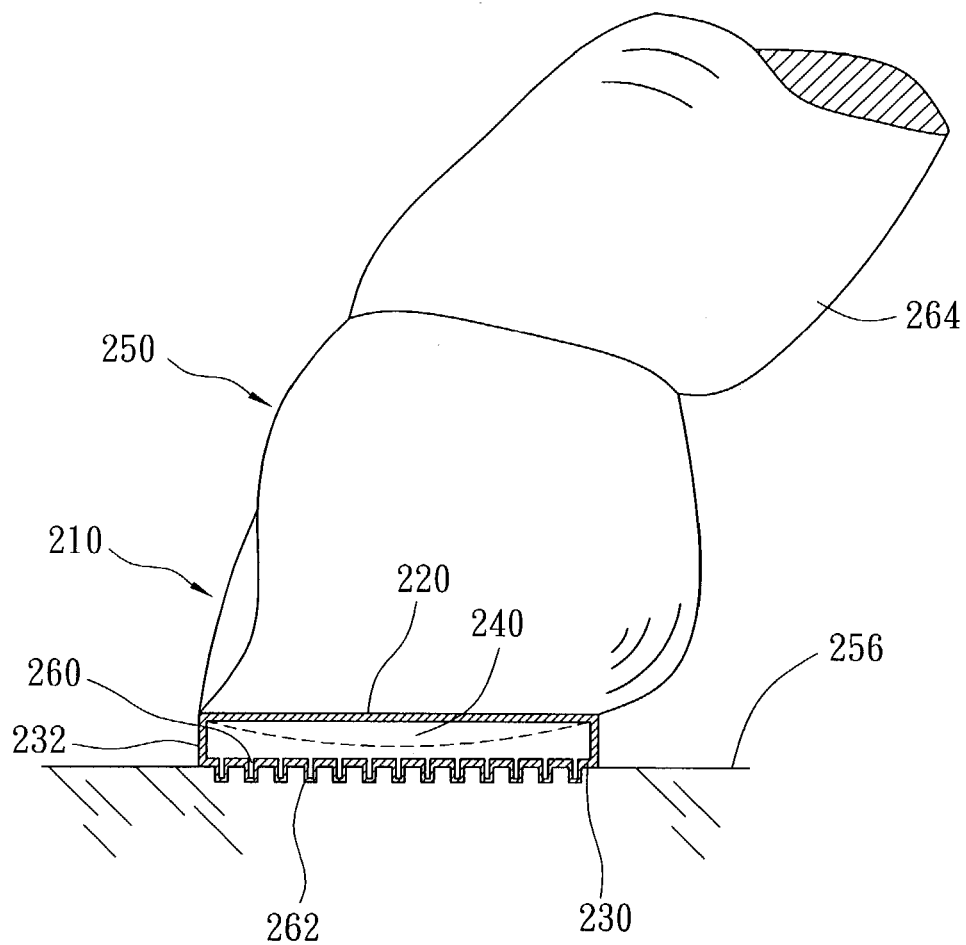
FIG. 2A is a simple schematic drawing depicting a micro apparatus according to U.S. Pat. No. 20020082543
Figure 2B:
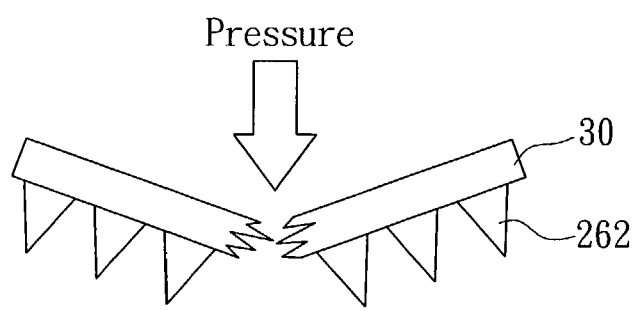
FIG. 2B is a simple schematic drawing depicting the substrate 230 of FIG. 2A while subjecting to an external force.
Figure 3A:
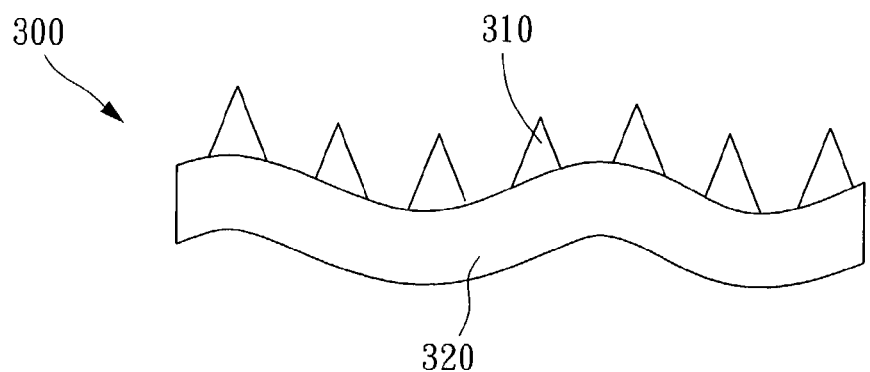
FIG. 3A is a simple schematic drawing illustrating a preferred embodiment of flexible substrate structure for microneedle arrays according to the present invention.
Figure 3B:
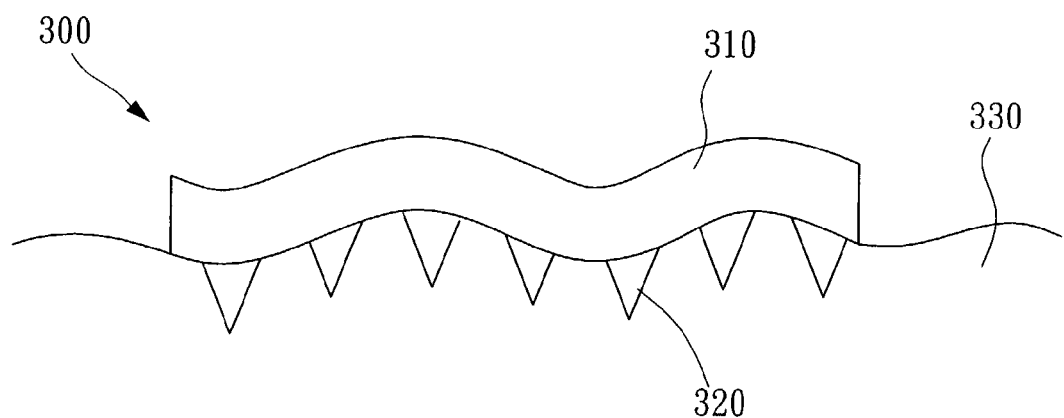
FIG. 3B is a simple application drawing illustrating a preferred embodiment of flexible substrate structure for microneedle arrays according to the present invention.

Please refer to FIG. 3A and FIG. 3B simultaneously. FIG. 3A is a simple schematic drawing illustrating a preferred embodiment of flexible substrate structure for microneedle arrays according to the present invention and FIG. 3B is a simple application drawing illustrating a preferred embodiment of flexible substrate structure for microneedle arrays according to the present invention. When tapered shape object 310 of microneedle arrays structure 300 is set up on flexible substrate 320, such as silicon rubber, polymethyl methacrylate (PMMA), polydimethyl siloxane (PDMS), polyethylene (PE), polypropylene (PP), etc. with reference to FIG. 3A, because the microneedle arrays structure 300 can be easily deformed, hence, the microneedle arrays structure 300 with reference to FIG. 3B can easily attaches itself to a rough surface 330, such as skin.

In addition to employ flexible material as substrate for microneedle arrays structures, different tapered shape objects can be used in cooperation with the flexible substrate depending on different requirements. For instance, a flexible substrate structure of microneedle array for backside drug delivery requires an opening on tip of its taped shape object structure so that the medicine can be delivered through backside of substrate by way of the openings of its tapered shape objects. Take a flexible substrate structure of microneedle array for human body signals detection as another example, the structure of its tapered shape object is plated with a conducting layer on its sidewalls and base surface so that human body signals can be transmitted from sidewalls of tapered shape objects to bases of tapered shape objects and outputted therefrom.

Therefore, the present invention not only is different from the microneedle array structures adopting rigid substrates, but also the fabricating processes for microneedle array structures adopting flexible substrates of the present invention are different according to different requirements.

Please refer to FIG. 4A~I, which are simple schematic drawings depicting each procedure of a fabricating process for microneedle array structures adopting flexible substrates that is applicable to both backside drug delivery and human body signal detection. First, referring to FIG. 4A, a conducting layer 465, such as a metal layer may be plated adopting an evaporation method, on tapered shape object 400 which may comprises an opening 405 on its tip 403. Meanwhile, extends the conducting layer 465 from sidewall 410 surface 420 of tapered shape object 400 to base 430 surface 440 of tapered shape object 400, so that human body signals can be transmitted by way of the two ends of conducting layer 465 of tapered shape object 400.

Afterwards, prepares to carry on with an ion implantation on tip 403 of tapered shape object 400, sidewall 410 of tapered shape object 400 and base area 430 of tapered shape object that is close to sidewalls 410 of tapered shape object, in order to form the exterior of tapered shape object 400 later on.

Figure 4A:
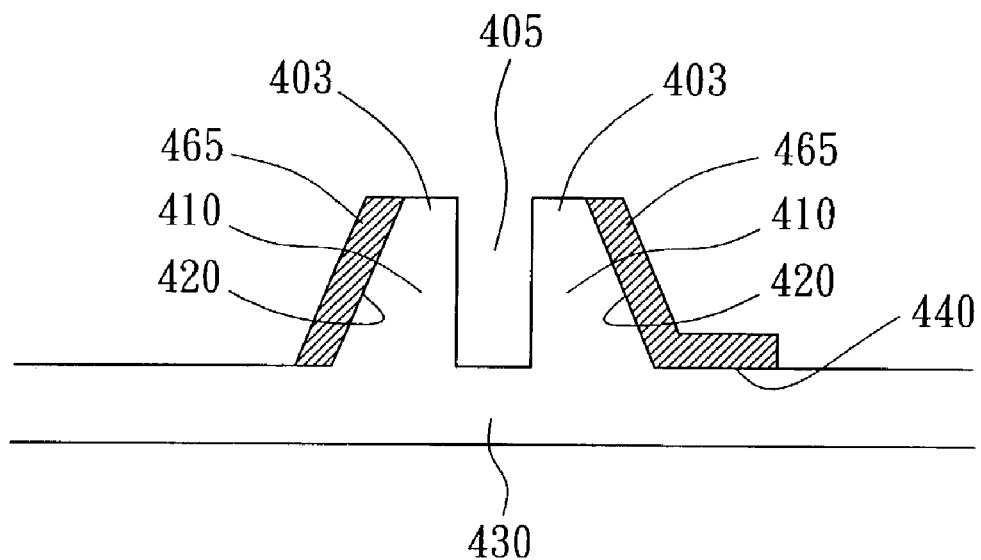
FIG. 4A~I are simple schematic drawings depicting each procedure of a fabricating process for microneedle array structures adopting flexible substrates that is applicable to both backside drug delivery and human body signal detection.
Figure 4B:
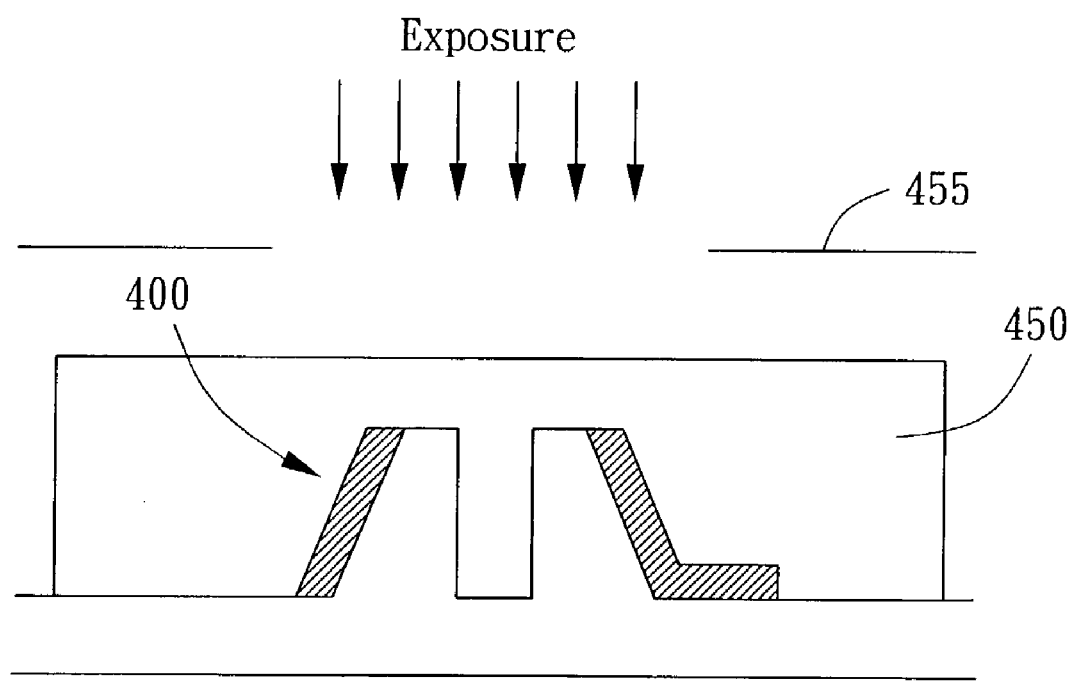
Figure 4C:
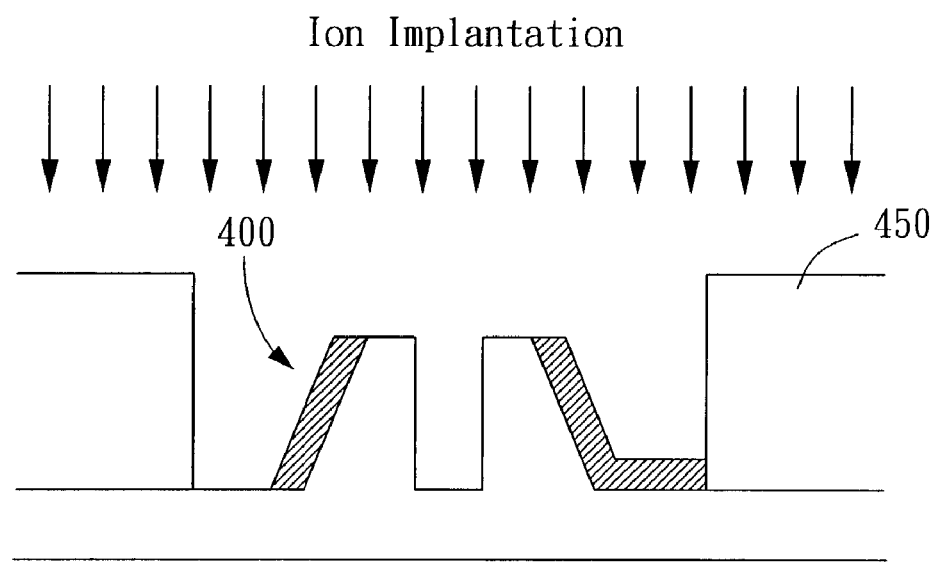
Figure 4D:
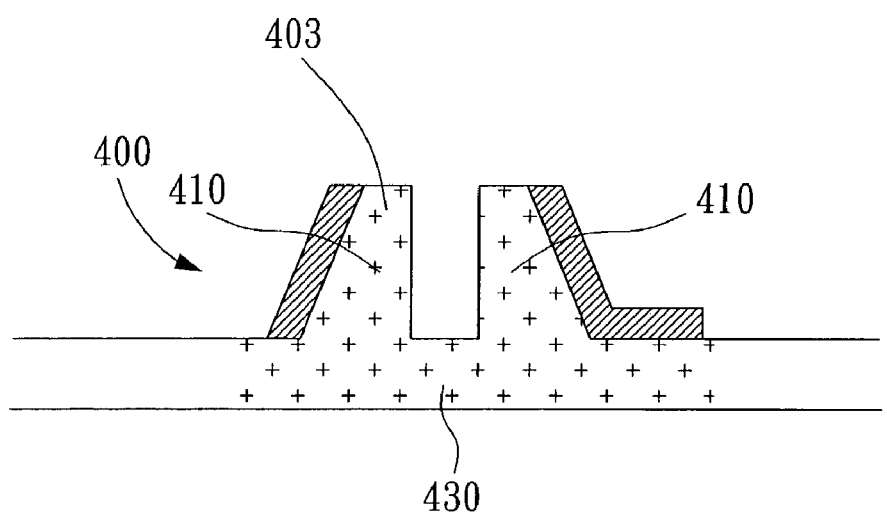

Those skilled in the art should appreciate that the ion implantation of the area can be achieved by procedures of semiconductor fabricating process, such as coating, exposure, development, photoresist strip, etc. Hence, as seen in FIG. 4B, at first a layer of photoresist 450 can be applied on surface of tapered shape object 400, then utilizes a photomask 455 to define an ion implantation area and carry on with an exposure procedure afterward. Then, further proceed with an ion implantation toward the remaining structures after exposure as seen in FIG. 4C. After the ion implantation, remove the photoresist on the tapered shape object 400. The result is that, as seen in FIG. 4D, the tapered shape object 400 only receives the ion implantation at its tip 403, sidewall 410 and base area 430 which is close to sidewall 410.

Figure 4E:
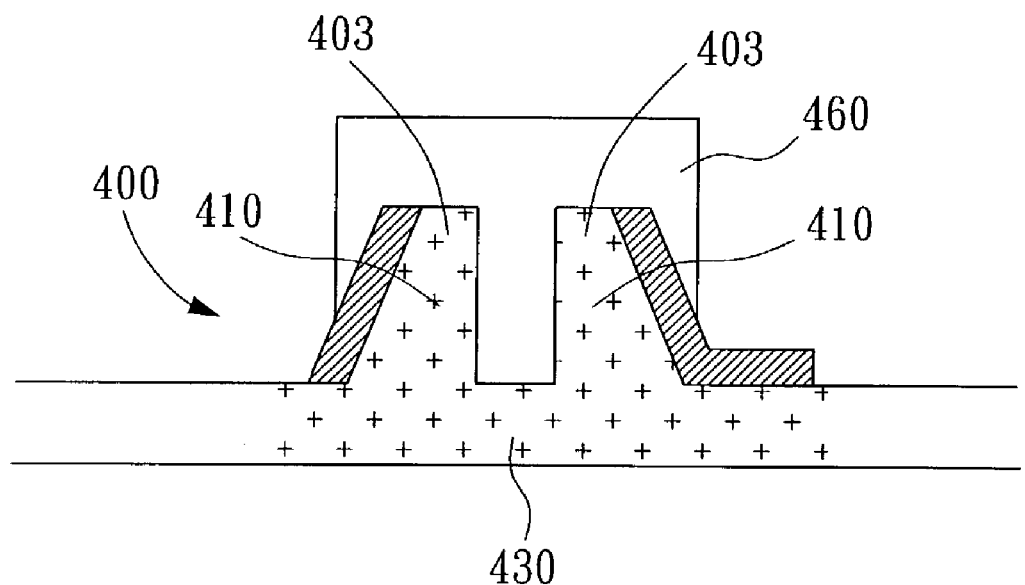
Figure 4F:
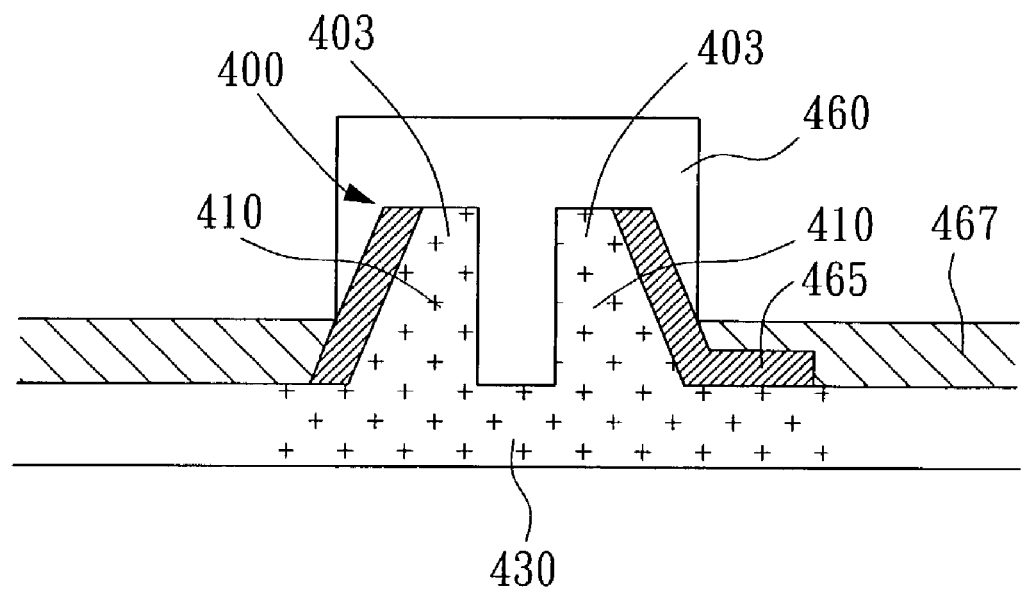
Figure 4G:
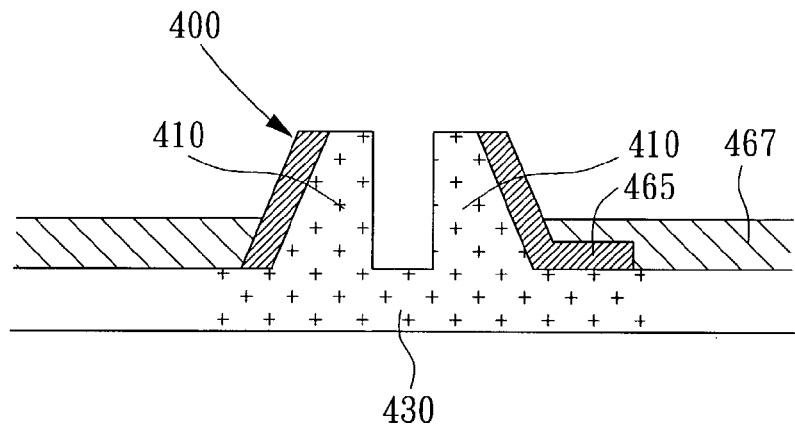

Next, prepare to apply a layer of flexible material as substrate on the base 430 of tapered shape object 400 facing the tip 403 of tapered shape object 400 and the conducting layer thereof, the same time, manage to enable the flexible substrate to wind tightly around the conducting layer on the sidewalls of tapered shape objects. In this way, the flexible material can be the substrate of tapered shape object and also firmly attaches itself to tapered shape object 400. Wherein, as seen in FIG. 4E, the method of FIG. 4C can be used first to form a layer of photoresist 460 on tip area 403 and part of sidewall area 410 of tapered shape object 400. Secondly, referring to FIG. 4F, apply a layer of flexible material 467 on the base 430 surface of tapered shape object 400 facing the tip 403 of tapered shape object 400, and the surface of the conducting layer 465 on part of sidewall 410. And, at a later time, remove the photoresist 460 from tapered shape object 400 in order to form a structure as seen in FIG. 4G.

Finally, when the flexible material on the tapered shape object is winded tightly around the conducting layer 465 on part of the sidewall 410 of tapered shape object 400 and is distributed on base 430, proceeds with an etching procedure on the tapered shape object 400. Because the tapered shape object itself contains ion implant on its tip 403, sidewall area 410 and base area 430 which close to sidewall 410, hence, while proceeding with an etching procedure on the tapered shape object 400, areas with ion implant and areas without ion implant will have different rate of etching. That is, the areas with ion implant on the base 430 of tapered shape object 400 will have a slower etching rate, and the areas without ion implant on the base 430 of tapered shape object 400 will have a faster etching rate.

Figure 4H:
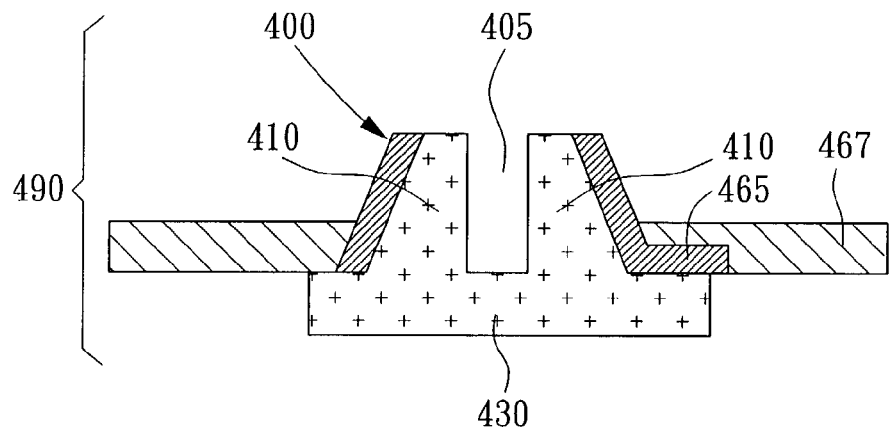

When finish etching the tapered shape object, the areas without ion implant on the base 430 of tapered shape object 400 will be etched completely, what's left is only the areas with ion implant which forms a final flexible substrate structure for microneedle array 490 according to a preferred embodiment of the present invention with reference to FIG. 4H.

Figure 4I:
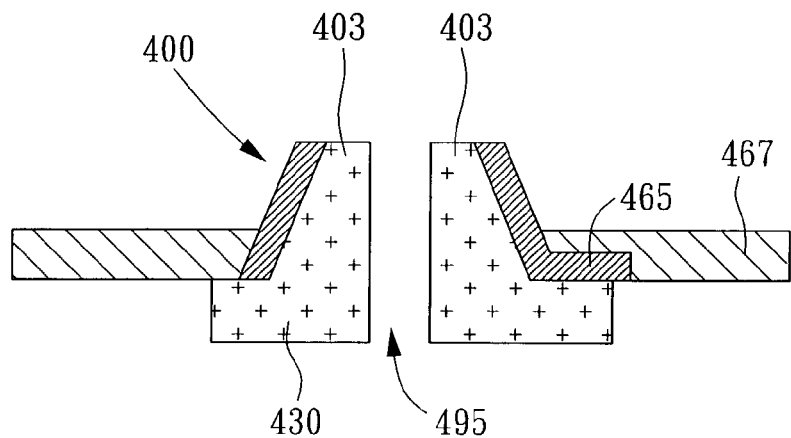

Therefore, the characteristics of a flexible substrate structure for microneedle array 490 according to a preferred embodiment of the present invention are:

1. The flexible substrate structure for microneedle array 490 is mainly the combination of tapered shape object 400 and flexible substrate 467 that is applicable to all kinds of surface.
2. The tapered shape object comprises a conducting layer 465, and the two ends of the conducting layer of the tapered shape object 400 is exposed on sidewall 410 of the tapered shape object 400 and between substrate 467 and base 430 which can be used respectively for detecting human body signals and outputting signals thereof.
3. If the etching time of FIG. 4g is increased, a structure can be formed as seen in FIG. 4I that an aperture 495 is formed between tip 403 of tapered shape object 400 and base 430 to accomplish a backside drug delivery device.
4. Because the present invention employs flexible materials as its substrate, hence, when a large-area fabrication is processed according to the present invention, the cracking condition is unlikely to happen.

The present invention provides a flexible substrate structure for microneedle arrays and its manufacturing method, which by way of the combination of tapered shape objects and flexible substrate, not only can increase its fit-to-body capability, but also enables thereof even more appropriate for backside drug delivery, as well as sufficiently bring the characteristic of large-area manufacturing into full play.

In summary that this invention has been disclosed and illustrated with reference to particular embodiments, the principles involved are susceptible for use in numerous other embodiments that will be apparent to persons skilled in the art. Consequently, the present invention has been examined to be progressive and has great potential in commercial applications.

Those skilled in the art should appreciate that they can readily use the disclosed conception and specific embodiments as a basis for designing or modifying other structures for carrying out the same purpose of the present invention, and that various changes, substitutions and alterations can be made herein without departing from the spirit and scope of the invention as defined by the append claims.

What is claimed is:

1. A method of fabricating a flexible substrate structure for microneedle arrays, which comprises the steps of:
    a) implanting ions on a tip, a sidewall, and a predetermined portion of a base of a tapered shape object to produce an ion implanted area of the tapered shape object, the side wall is located adjacent to the tip and the base;
    b) applying a flexible substrate on a lower part of a surface of the sidewall and a top surface of the base, the flexible substrate extending around a periphery of the sidewall;
    c) removing a portion of the base surrounding the ion implanted area utilizing an etching process to produce the flexible substrate structure having the flexible substrate connected to a top surface of the predetermined portion of the base and the lower portion of the sidewall, the ions located in the ion implanted area of the tapered shape object preventing etching of the ion implanted area during the etching process.

2. The method according to claim 1, wherein the implanting step a) is preceded by a step of plating a conducting layer on the sidewall and base of the tapered shape object, the conducting layer transmitting signals from a sidewall conducting layer portion located on the sidewall to a base conducting layer portion located on the base.

3. The method according to claim 2, wherein the step of plating is performed utilizing an evaporation method.

4. The method according to claim 1, wherein the implanting step a) includes the steps of:
    a1) applying a layer of photoresist on top surfaces of the tip, the sidewall, and the predetermined portion of a base of a tapered shape object;
    a2) exposing the photoresist and defining an area on the tapered shape object for ion implantation; and
    a3) implanting the ions on the tip, the sidewall, and the predetermined portion of a base of the tapered shape object to produce the ion implanted area of the tapered shape object.

5. The method according to claim 4, wherein the exposing and defining step a2) is performed utilizing a photomask to define the area on the tapered shape object for ion implantation.

6. The method according to claim 1, wherein the removing step c) includes the steps of:
    c1) applying a layer of photoresist on the tip and an upper portion of the sidewall of the tapered shape object;
    c2) removing the portion of the base of the tapered shape object surrounding the ion implanted area; and
    c3) removing the photoresist from the tapered shape object.

* * * * *